US007087336B2

(12) United States Patent
Fleck et al.

(10) Patent No.: US 7,087,336 B2
(45) Date of Patent: Aug. 8, 2006

(54) PROCESS FOR PRODUCING A SOLID ELECTROLYTE LAYER ON A SUBSTRATE, IN A FUEL CELL, AND IN A SENSOR

(75) Inventors: Robert Fleck, Adelsdorf (DE); Michael Kuznecov, Dresden (DE); Peter Otschik, Possendorf (DE); Winfried Schaffrath, Dresden (DE); Nikolai Trofimenko, Dresden (DE)

(73) Assignee: Fraunhofer Gesellschaft zur Foerderung der Angewandten Forschung e.V., Munich (DE)

( * ) Notice: Subject to any disclaimer, the term of this patent is extended or adjusted under 35 U.S.C. 154(b) by 160 days.

(21) Appl. No.: 10/373,322

(22) Filed: Feb. 24, 2003

(65) Prior Publication Data

US 2003/0148163 A1 Aug. 7, 2003

Related U.S. Application Data

(63) Continuation of application No. PCT/EP01/09761, filed on Aug. 23, 2001.

(30) Foreign Application Priority Data

Aug. 24, 2000 (EP) .................................. 00118429

(51) Int. Cl.
*H01M 8/12* (2006.01)
*B05D 5/12* (2006.01)
*C04B 35/64* (2006.01)

(52) U.S. Cl. ..................... 429/33; 427/115; 427/126.3; 204/424; 264/618

(58) Field of Classification Search ................. 429/33; 427/115, 126.3; 204/424; 264/618
See application file for complete search history.

(56) References Cited

U.S. PATENT DOCUMENTS

| 4,303,447 A | 12/1981 | Buchanan et al. |
| 4,764,491 A | 8/1988 | Quadir |
| 5,171,645 A * | 12/1992 | Khandkar ..................... 429/33 |

FOREIGN PATENT DOCUMENTS

EP 0 414 575 A1 2/1991

(Continued)

OTHER PUBLICATIONS

V.K. Gil'derman et al.: "Effect of small additions of electrically conductive oxides on the oxygen permeability of a zirconium dioxide+yttrium sesquioxide ($0.9ZrO_2$ + $0.1Y_2O_3$) solid electrolyte", *Chemical Abstracts 86: 9906H*, vol. 86, Oct. 1, 1977, No. 2, XP-002158608.

(Continued)

*Primary Examiner*—Jonathan Crepeau
(74) *Attorney, Agent, or Firm*—Laurence A. Greenberg; Werner H. Stemer; Ralph E. Locher

(57) ABSTRACT

A method for producing a solid electrolyte layer, of a fully stabilized zirconium oxide layer on a substrate includes adding a sintering additive to a ZrO2-starting material, a liquid phase is formed during a sintering process and liquid phase sintering is possible at a reduced temperature in comparison with the required sintering temperature without the sintering additive. The reduced sintering temperature substantially prevents the formation of a foreign phase layer between the substrate and the gas-tight layer applied thereon, being of fully stabilized ZrO2. The method is particularly suitable for producing a solid electrolyte layer on a cathode of a high temperature fuel cell and in a sensor.

37 Claims, 4 Drawing Sheets

FOREIGN PATENT DOCUMENTS

JP    64 003 070    1/1989

OTHER PUBLICATIONS

R.C. Buchanan et al.: "Densification of Submicron YSZ Powders With Alumina and Borate Additives", Technical Final Report No. 9, Contract US NAVY-N-00014-80-K-0969, vol. 85, No. 8, Dec. 1984, pp. 1-41, XP-001051439.

S. Ramesh et al.: "The effect of copper oxide on sintering, microstructure, mechanical properties and hydrothermal ageing of coated 2.5Y-TZP ceramics", *Journal of Materials Science*, No. 34, 1999, pp. 5457-5467, XP-000978655.

* cited by examiner

PROCESS FOR PRODUCING A SOLID ELECTROLYTE LAYER ON A SUBSTRATE, IN A FUEL CELL, AND IN A SENSOR

CROSS-REFERENCE TO RELATED APPLICATION

This application is a continuation of copending International Application No. PCT/EP01/09761, filed Aug. 23, 2001, which designated the United States and was not published in English.

BACKGROUND OF THE INVENTION

Field of the Invention

The invention relates to a process for producing a solid electrolyte layer, made of a fully stabilized zirconium oxide layer, on a substrate, in a fuel cell, and in a sensor.

The solid electrolyte layer made from fully stabilized zirconium oxide ($ZrO_2$) is used as an ion-conducting layer in many technical fields. In general, the aim is to achieve a solid electrolyte layer that is as dense as possible. This applies, for example, to the field of power engineering, in this case particularly with regard to a high-temperature fuel cell, and to sensors, and, in particular, the field of gas sensors.

The term fully stabilized zirconium oxide is understood as meaning the stable cubic phase of zirconium oxide. To obtain the cubic phase, the zirconium oxide is doped with an oxide of one of the rare earths, in particular, with yttrium oxide. In this case, approximately 8 to 12 mol % of yttrium oxide is added to the zirconium oxide to ensure that the zirconium oxide is present in the stable cubic phase regardless of the temperature. Compared to the tetragonal or monoclinic phase of the zirconium oxide, the cubic phase has a significantly higher ion conductivity. Therefore, the cubic phase is desired for the solid electrolyte layer, as is disclosed, for example, from European Patent Application 0 414 575 A1, corresponding to U.S. Pat. No. 5,130,210 to Iwasaki et al. This application proposes that metal oxides be incorporated in the fully stabilized zirconium oxide to increase the ion conductivity.

In addition to the fully stabilized zirconium oxide, what is referred to as partially stabilized zirconium oxide, which is stabilized with just 2 to 2.5 mol % of yttrium oxide, is used as a coating material in many technical application areas.

The partially stabilized zirconium oxide is in the tetragonal phase, which, although it has improved properties particularly with regard to the mechanical breaking strength and the respective thermal shock resistance, also has a worse ion conductivity and is, therefore, unsuitable as a solid electrolyte layer. In any case, in terms of the tetragonal phase it must be ensured that there is no phase transformation from the tetragonal phase to the monoclinic phase. The article "The effect of copper oxide on sintering, micro-structure, mechanical properties and hydrothermal ageing of coated 2.5Y-TZP ceramics" by S. Ramesh et al, Journal of Materials Science, Volume 34, No. 22, 1999, pp. 5457 to 5467, discusses the effect of adding various quantities of copper oxide as sintering additive to initiate liquid-phase sintering in order to suppress the phase transformation from the tetragonal phase into the monoclinic phase.

To produce the gastight solid electrolyte layer, the solid electrolyte material is conventionally applied to the substrate that is to be coated using an electrochemical vapor deposition (EVD) process. Although the EVD process achieves a good layer quality, this process is very expensive. Alternative coating processes, such as plasma spraying processes and sintering processes, have hitherto produced $ZrO_2$ solid electrolyte layers that are not as good.

In the fuel cell, the $ZrO_2$ layer is applied to one of the two electrodes of the fuel cell, in particular, to the cathode. The $ZrO_2$ layer is used as an electrolyte layer between the two electrodes. In the fuel cell, the electrodes have porous configuration. To generate electrical energy, a fuel gas, for example, hydrogen, is passed over one electrode and air or oxygen is passed over the other electrode.

Ion exchange between the fuel and the oxygen takes place through the electrolyte layer so that an electric voltage is formed between the two electrodes. Therefore, the $ZrO_2$ layer as a solid electrolyte layer must, on one hand, have a good ion conductivity and, on the other hand, be substantially gastight to avoid direct contact between fuel gas and oxygen.

SUMMARY OF THE INVENTION

It is accordingly an object of the invention to provide a process for producing a solid electrolyte layer on a substrate, in a fuel cell, and in a sensor that overcomes the hereinaforementioned disadvantages of the heretofore-known devices and methods of this general type and that provides a cost-effective process for producing a high-quality solid electrolyte layer.

With the foregoing and other objects in view, there is provided, in accordance with the invention, a method for producing a solid electrolyte layer, of a fully stabilized zirconium oxide layer on a substrate, including the steps of applying a zirconium oxide starting material to the substrate together with a sintering additive as a green layer, the sintering additive being boron nitride, bismuth oxide, or a combination of these compounds, forming a liquid phase of the sintering additive by subsequently heating the sintering additive, and densifying the green layer with a liquid-phase sintering operation at a reduced sintering temperature as compared to a sintering temperature required without the sintering additive.

With the objects of the invention in view, there is also provided a method for producing a solid electrolyte layer, of a fully stabilized zirconium oxide layer on a substrate, including the steps of applying a zirconium oxide starting material to the substrate together with a sintering additive as a green layer, forming a liquid phase of the sintering additive by subsequently heating the sintering additive, and densifying the green layer to form a densified layer with a liquid-phase sintering operation at a reduced sintering temperature compared to a sintering temperature required without the sintering additive, in which operation process parameters, including at least one of heating rate, sintering temperature, and holding time, are selected to cause the liquid phase to still be present when the reduced sintering temperature is reached and to cause the densified layer to be substantially free of the sintering additive, the reduced sintering temperature being higher than a sintering temperature required for a sintering operation with sintering additive.

With the objects of the invention in view, there is also provided a method for producing a solid electrolyte layer, of a fully stabilized zirconium oxide layer on a substrate, including the steps of applying to the substrate a zirconium oxide starting material as a green layer with the sintering additive and a zirconium oxide starting material as a green layer without the sintering additive, forming a liquid phase of the sintering additive by subsequently heating the sintering additive, and densifying the green layer with a liquid-phase sintering operation at a reduced sintering temperature compared to a sintering temperature required without the sintering additive.

According to the invention, a process for producing a solid electrolyte layer, of a fully stabilized and, in particular, gastight $ZrO_2$ layer, on a substrate, includes:

- a $ZrO_2$ starting material, together with a sintering additive, is applied as a green layer to the substrate;
- the sintering additive forms a liquid phase as a result of subsequent heating; and
- the green layer is densified by a liquid-phase sintering step carried out at a reduced sintering temperature compared with the sintering temperature required without the sintering additive.

On account of the sintering process, the process allows extremely cost-effective production of the fully stabilized $ZrO_2$ layer, which is provided, in particular, with 8–12 mol % of $Y_2O_3$ (yttrium oxide), as solid electrolyte layer. The low sintering temperature, at the same time, leads to the formation of a high-quality solid electrolyte layer, the quality of which is comparable to that of a solid electrolyte layer applied by an EVD process.

In such a context, the main point is considered to reside in the fact that liquid-phase sintering at a reduced sintering temperature is made possible by the addition of a suitable sintering additive. Consequently, the sintering, i.e., the densification, of the green layer takes place at relatively low temperatures.

The invention is based on the discovery that when the solid electrolyte layer is produced by conventional sintering processes, a problem of a foreign phase layer forming between the substrate and the actual gastight layer on account of the high sintering temperatures of 1,400° C. required for $ZrO_2$ arises. This represents a significant drawback, in particular, in the field of high-temperature fuel cells because the foreign-phase layer that is formed during the conventional sintering process impedes ion conduction and leads to a low fuel cell efficiency. On account of the sintering temperature being lower than the "normal" sintering temperature for $ZrO_2$ of approximately 1,400° C., the formation of a foreign-phase layer is substantially suppressed. The formation of the foreign-phase layer, as a thermodynamic process, is greatly dependent on the temperature.

The term green layer or green body is understood in a general sense as meaning the specimen that has been prepared for sintering. Such a green body includes, by way of example, in addition to the $Zr_2O$ powder that is doped, for example, with 8–12 mol % of $Y_2O_3$, also a binder and has a relatively high moisture content so that it can be shaped and worked.

According to an advantageous configuration, the sintering additive added is boron nitride (BN), bismuth oxide ($BiO_2$), copper oxide (CuO), or a combination of these compounds. These compounds are suitable particularly advantageously for reducing the sintering temperature through the formation of a liquid phase. In such a context, boron nitride, which is oxidized in air during the sintering process to form boron oxide ($B_2O_3$), has proven particularly suitable.

$B_2O_3$ is in the form of a liquid phase even at temperatures of above approximately 400° C. and is responsible for partial $ZrO_2$ dissolution and $ZrO_2$ transportation within the layer, which has a beneficial effect on the sintering, i.e., the densification. Therefore, it is preferable for $B_2O_3$ to be used directly as the sintering additive.

It is expedient for approximately between 0.5 and 3% by weight of sintering additive to be added. This range has proven suitable for promoting the liquid-phase sintering at a reduced sintering temperature.

In accordance with another mode of the invention, it is preferable for the process parameters, such as heating rate, sintering temperature, and holding time, to be selected such that, when the reduced sintering temperature is reached, the liquid phase is still present, and that the densified layer is substantially free of sintering additive at the end of the sintering process. This ensures that, on one hand, liquid-phase sintering at reduced temperature is ensured, and, therefore, the formation of a foreign-phase layer is substantially prevented. On the other hand, the fully sintered, gastight layer does not include any residues of the sintering additive that could have an adverse effect on the properties of the layer.

In such a case, it is preferable to set a maximum sintering temperature of less than 1,400° C. and, in particular, of less than 1,300° C. It is expedient for the sintering temperature to be between 1,100° C. and 1,300° C. Densification already takes place at these temperatures, on account of the presence of the liquid phase, and the formation of a foreign-phase layer is also suppressed at these temperatures.

In accordance with a further mode of the invention, it is expedient to set a heating rate of from 4 to 7 K/min.

In accordance with an added mode of the invention, a green layer that includes sintering additive and a $ZrO_2$ layer that does not include sintering additive is to be applied to the substrate. The two layers are, therefore, present in stratified form on the substrate. The $ZrO_2$ layer that does not include sintering additive may, likewise, be formed as a green layer or may already have been presintered. During the subsequent full sintering, the two layers bond with one another to form a homogeneous gastight layer. The stratified structure has a beneficial effect on the sintering process and results in a good sintering result being achieved.

In accordance with an additional mode of the invention, it is advantageous for a fully sintered $ZrO_2$ layer with a porosity of less than 5% by volume to be formed. The porosity is, therefore, lower than the porosity of a conventionally sintered layer by at least a factor of 2.

In accordance with yet another mode of the invention, it is expedient to apply a layer thickness of between 5 and 100 μm. This, on one hand, ensures a mechanically stable coating while, on the other hand, achieves good electrochemical properties and a high gas impermeability, which is important for use in a fuel cell.

In accordance with yet a further mode of the invention, a gastight layer is formed with an air permeability (leak rate) of $\leq 10^{-3}$ mbar·l/s·cm$^2$, and, in particular, of approximately $2·10^{-4}$ mbar·l/s·cm$^2$. Therefore, the air permeability is below that achieved in a conventional sintering process by approximately two (2) orders of magnitude. At the same time, an air impermeability that is comparable to the air impermeability that can be achieved by an EVD process is achieved.

The process with the addition of a suitable sintering additive for reducing the sintering temperature by promoting liquid-phase sintering, therefore, makes it possible to form a gastight layer, which, in terms of quality, is comparable to a layer produced by EVD but is considerably less expensive than the EVD process.

With the objects of the invention in view, there is also provided a fuel cell, including an electrode and a fully stabilized zirconium oxide layer produced according to the process of the invention as a solid electrolyte layer coating the electrode.

With the objects of the invention in view, there is also provided a gas sensor, including a sensor component and a fully stabilized zirconium oxide layer produced according to the process of the invention as a solid electrolyte layer applied to the sensor component.

Other features that are considered as characteristic for the invention are set forth in the appended claims.

Although the invention is illustrated and described herein as embodied in a process for producing a solid electrolyte layer on a substrate, in a fuel cell, and in a sensor, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
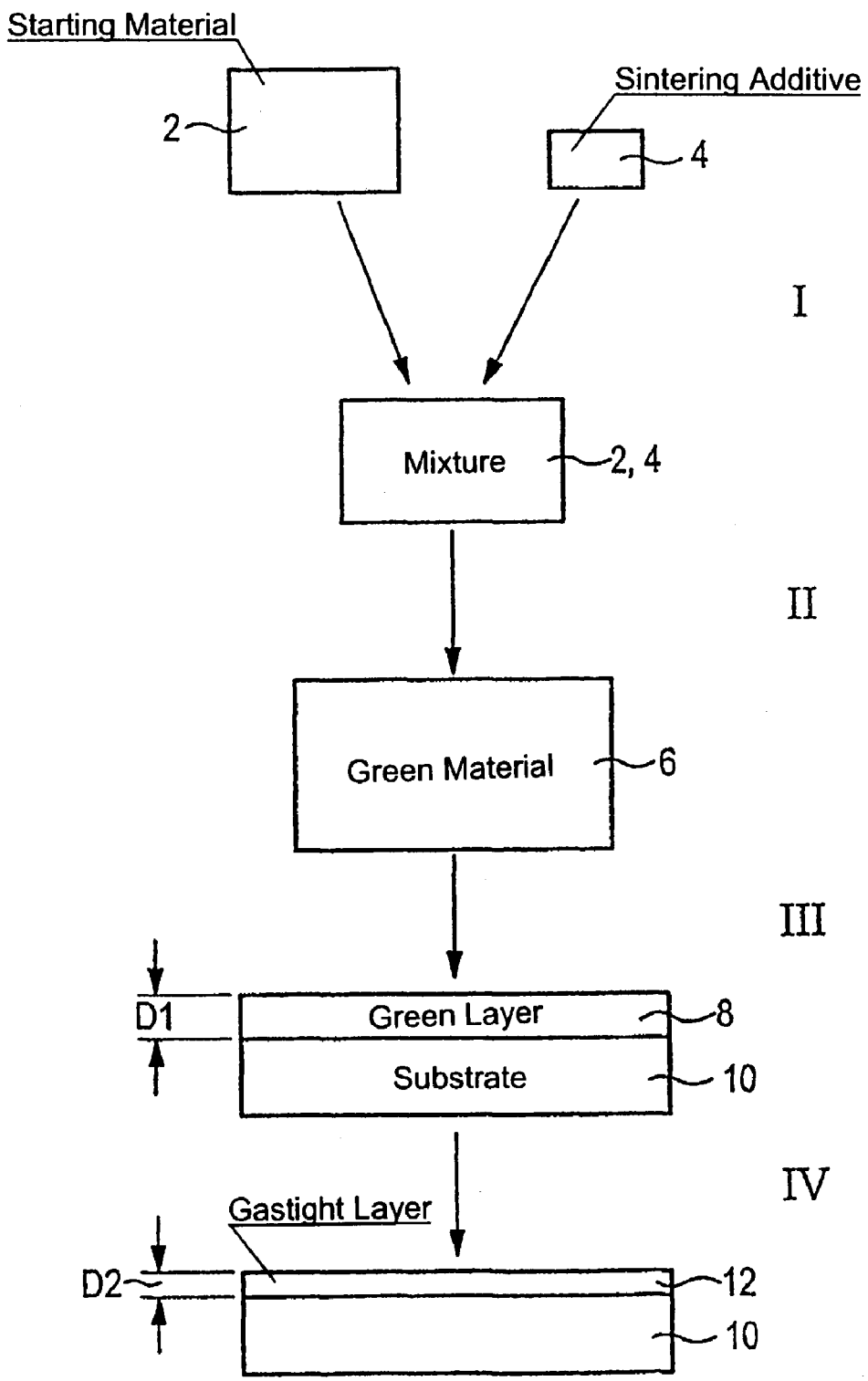
FIG. 1 is a flow chart and diagrammatic illustration of a process sequence for applying a gas-tight $ZrO_2$ layer according to the invention.

Referring now to the figures of the drawings in detail and first, particularly to FIG. 1 thereof, there is shown a process sequence where a $ZrO_2$ starting material 2 and a sintering additive 4, in particular, boron nitride, are mixed with one another in a mixing vessel in a first process step I. Both the sintering additive 4 and the $ZrO_2$ starting material are, preferably, in powder form. A $ZrO_2$ starting material is, in this case, understood to mean a powder mixture of $ZrO_2$ with additions of usually 8–12 mol % of yttrium oxide ($Y_2O_3$) and/or magnesium oxide (MgO) and/or calcium oxide (CaO). Aluminum oxide ($Al_2O_3$) and cerium oxide ($CeO_2$) can be added as further additions. These additions lead to the formation of what is referred to as a fully stabilized, gastight $ZrO_2$ layer.

In a second process step II, the powder mixture of $ZrO_2$ and boron nitride is dispersed and worked into a workable paste, what is known as the green material 6. For such a purpose, in particular, water and binder are fed to the powder mixture.

In a third process step III, the green material 6 is applied to a substrate 10 as green layer 8. This takes place, for example, by a screen-printing process, slip casting, pressure filtration, or vacuum slip casting, which is a particular variant of slip casting. Depending on the consistency, the green material 6 can also be applied to the substrate 10 by wet-powder spraying. The green layer 8 has, for example, a green thickness D1 of 80 μm and a porosity of approximately 50% by volume.

In the following process step 4, the substrate 10 together with the green layer 8 that has been applied to it is heated up to a maximum sintering temperature of 1,300° C. at a heating rate of between 4 and 7 K/min and is sintered at the sintering temperature for approximately 5 hours so that a gastight layer 12 of fully stabilized zirconium oxide is formed. On account of the shrinkage that occurs during sintering, the gastight layer 12 has a layer thickness D2 of only approximately 30 to 40 μm after the sintering. A porosity of the gastight layer 12 is less than 5% by volume. Its air permeability, also referred to as the leak rate, is approximately $2 \cdot 10^{-4}$ mbar·l/s·cm$^2$. The determination of the leak rate is based on DIN 28402.

In the process, liquid-phase sintering of $ZrO_2$ is initiated by the addition of the sintering additive 4, in particular, boron nitride. As a result, the sintering temperature required to sinter $ZrO_2$ is lowered (reduced sintering temperature). At the same time, the low viscosity means that no stresses or only minor stresses are produced in the layer that is to be applied during the liquid-phase sintering.

In the process, during the heating of the green layer 8, the BN is oxidized in air to form $B_2O_3$ at temperatures of over 800° C. $B_2O_3$ is already present as a liquid phase even at temperatures over 400° C. The $B_2O_3$ liquid phase causes partial dissolution of the $ZrO_2$ and also allows $ZrO_2$ to be transported within the layer even at the reduced sintering temperature. Therefore, the densification of the layer takes place even at temperatures between 1,100° C. and 1,300° C., i.e., well below the sintering temperature that is normally required for $ZrO_2$ of approximately 1,400° C. without a suitable sintering additive 4. At the same time, the temperatures above approximately 1,100° C. during the sintering process lead to the evaporation of the $B_2O_3$ and to $ZrO_2$ being precipitated again out of the liquid phase. With the process parameters given above, at the end of the sintering process, substantially all the $B_2O_3$ has escaped from the layer 12. Accordingly, there are no boron-containing residues left in the layer 12 after the sintering has taken place.

Figure 2:
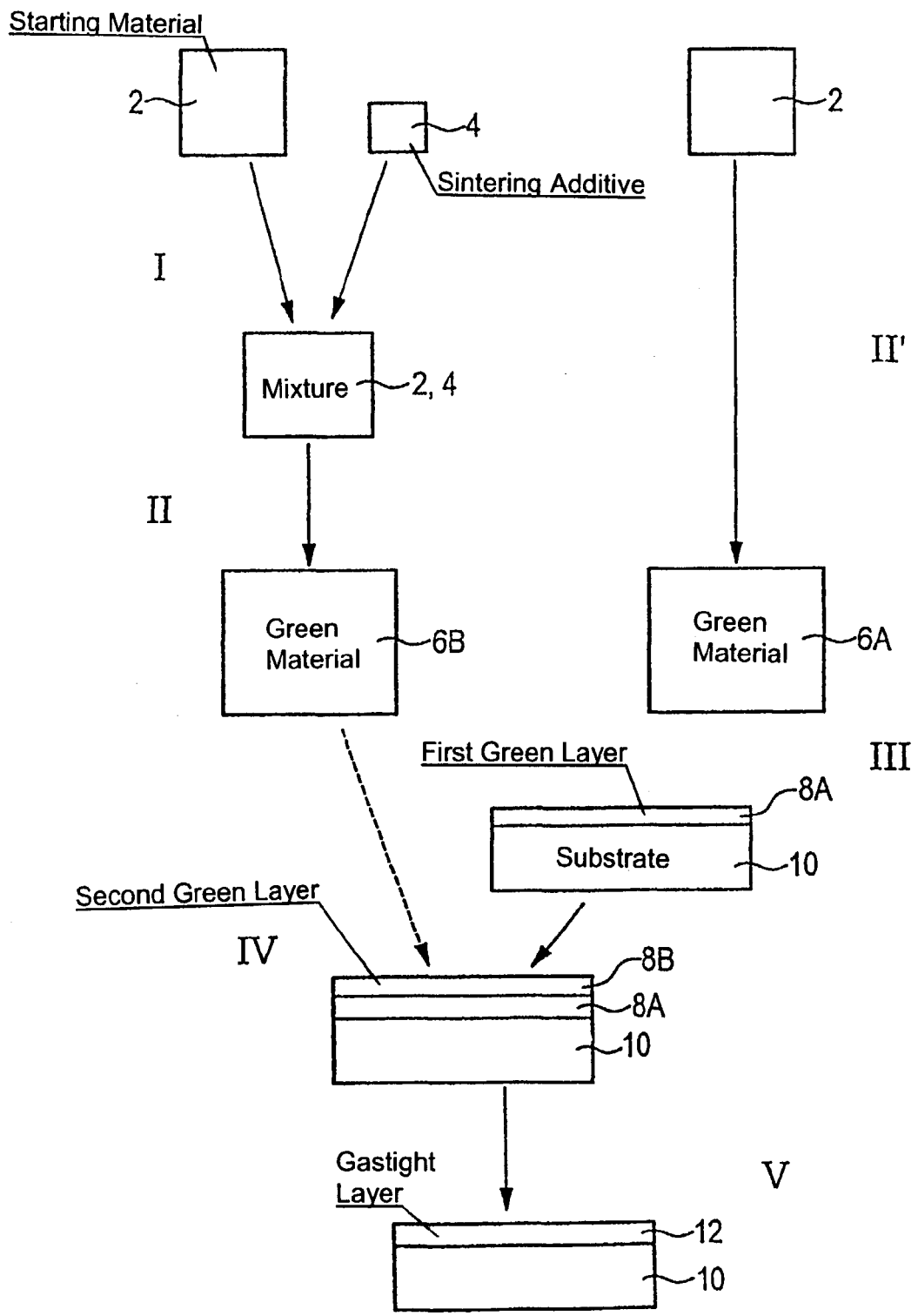
FIG. 2 is a flow chart and diagrammatic illustration of an alternative embodiment of the process sequence of FIG. 1.

In a modified process sequence shown in FIG. 2, two different layers are applied to the substrate 10 in process steps III and IV prior to the actual sintering process (process step V). Specifically, first of all, a first green layer 8A including $ZrO_2$ green material 6A without sintering additive 4 is applied to the substrate 10. Then, a second green layer 8B that includes the sintering additive 4 is applied to the first green layer 8A that is free of sintering additive. The green material 6B used for the second green layer 8B is obtained in a similar way to that which has been described in process steps I and II in FIG. 1. The green material 6A that is free of sintering additive is prepared in a process step II' that corresponds to process step II. Following the application of the second green layer 8B, the actual sintering takes place in process step V, as has already been described in connection with FIG. 1.

Alternatively, the first green layer 8A, which is free of sintering additive, may undergo sintering or presintering after the first green layer 8A has been applied. Then, the second green layer 8B is applied to the $ZrO_2$ layer, which has now been presintered, and is, then, sintered.

Because the sintering additive 4 escapes during the sintering process, in both alternative cases a homogeneous and uniform gastight layer 12 is formed on the substrate 10.

Figure 3:
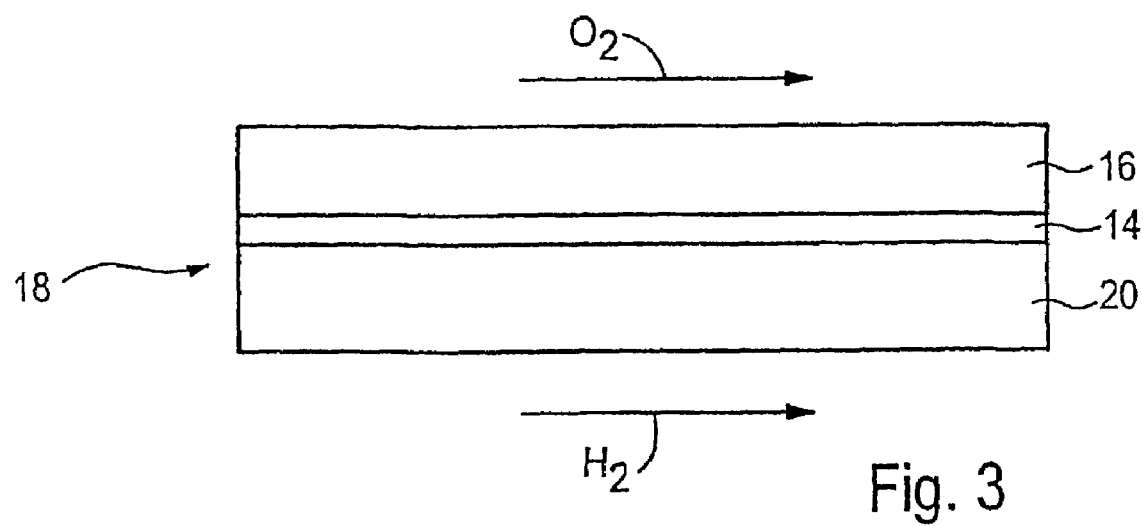
FIG. 3 is a diagrammatic illustration of a planar high-temperature fuel cell according to the invention.

Such a process for applying a gastight $ZrO_2$ layer 12 is particularly suitable for applying a $ZrO_2$ electrolyte layer 14 to an electrode, in particular, to the cathode 16 of a high-temperature fuel cell 18, as illustrated in greatly simplified form in a planar configuration in FIG. 3.

As an alternative to the planar configuration, tubular fuel cells 18 are also available. In such cells, the solid electrolyte layer 14 is enclosed between an inner cathode tube and an outer anode tube. The green layer 8, which forms the solid electrolyte layer 14 after it has been sintered, is applied to the cathode tube, for example, by cylindrical screen printing. A porous perovskite material ($La_{1-x}Ca_xMnO_3$) is generally used as the material of the cathode 16 and the anode 20.

In the case of the fuel cell 18, the solid electrolyte layer 14 is disposed between the cathode 16 and the anode 20. When the fuel cell 18 is operating, air or oxygen $O_2$ passes over the cathode 16, and fuel gas, for example, hydrogen $H_2$, passes over the anode 20. Oxygen ions are transferred from the air-gas side to the fuel-gas side through the electrolyte layer 14, and an electric voltage is generated.

To achieve a high efficiency in the fuel cell 18, the electrolyte layer 14, on one hand, has to be as gastight as possible to prevent direct contact between the oxygen and the fuel gas. On the other hand, the layer 14 must have a good oxygen ion conductivity. This firstly requires the zirconium oxide to be in the cubic phase, i.e., to be fully stabilized. However, the oxygen ion conduction would be adversely affected by the formation of a foreign-phase layer between the cathode 16 and the solid electrolyte layer 14, as is formed in a conventional sintering process.

Compared to conventional sintering processes, the processes described in connection with FIGS. 1 and 2 have the crucial advantage that, on account of the relatively low sintering temperature, the formation of such a foreign-phase layer is substantially suppressed. The sintered solid electrolyte layer 14 has similar electrical properties to a layer produced using the significantly more expensive EVD process.

Figure 4:
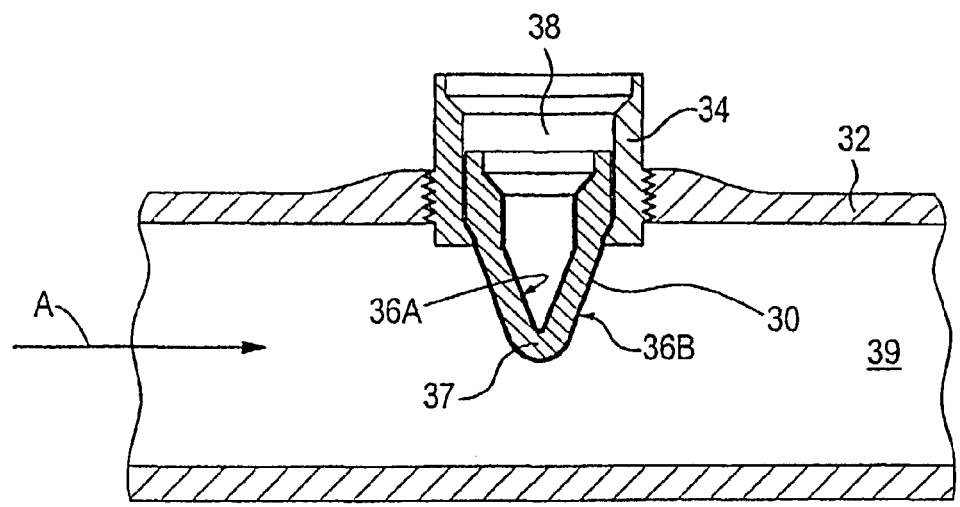
FIG. 4 is a fragmentary, cross-sectional view of a gas sensor according to the invention configured as a $\lambda$ probe in a line.

A further application area for the process for applying the gastight $ZrO_2$ layer 12 is that of sensors, in particular, gas sensors for determining an oxygen content in a gas. The gas sensor 30, which, in accordance with FIG. 4, is constructed as a λ probe, is used, in particular, to determine the oxygen content in the exhaust gas A from a motor vehicle. The gas sensor 30 for this purpose extends into an exhaust pipe 32, through which the exhaust gas A is flowing. The sensor 30 is attached to the exhaust pipe 32 by a holder 34. In terms of its basic structure, the gas sensor 30 is similar to the fuel cell 18 and has a solid electrolyte layer 37, which is formed as a gas-tight $ZrO_2$ layer, between an inner electrode 36A and an outer electrode 36B. The two electrodes 36A, 36B are porous, the inner electrode 36A being oriented toward a comparison gas space 38 and the outer electrode 36B being oriented toward the exhaust gas space 39. The oxygen ion conduction is used to determine the oxygen content in the exhaust gas A, in a similar way to in the fuel cell 18. If there is a different oxygen concentration in the comparison gas space 38 and the exhaust gas space 39, oxygen ion conduction takes place through the solid electrolyte layer 37, and a voltage is formed. If the oxygen concentration in the comparison gas space 38 is known, the oxygen content in the exhaust gas A can be determined from the measured voltage.

To determine the leak rate or air permeability of the gastight layer 12, in accordance with DIN 28402, the pV flow (p: pressure; V: volume) of a gas through the layer 12 is determined. In the process, a defined differential pressure is applied between the two sides of the gastight layer 12. The leak rate $q_L$ (or the specific leak rate $q_{LF}$) is determined according to the following formulae:

$$q_L = dp/dt \cdot V [mbar \cdot l/s \cdot cm^2]; \text{ and}$$

$$q_{LF} = dp/dt \cdot V/F [mbar \cdot l/s \cdot cm^2],$$

where F is the area to be tested and dp is the pressure increase or pressure drop in the measurement time dt in the volume V.

Figure 5:
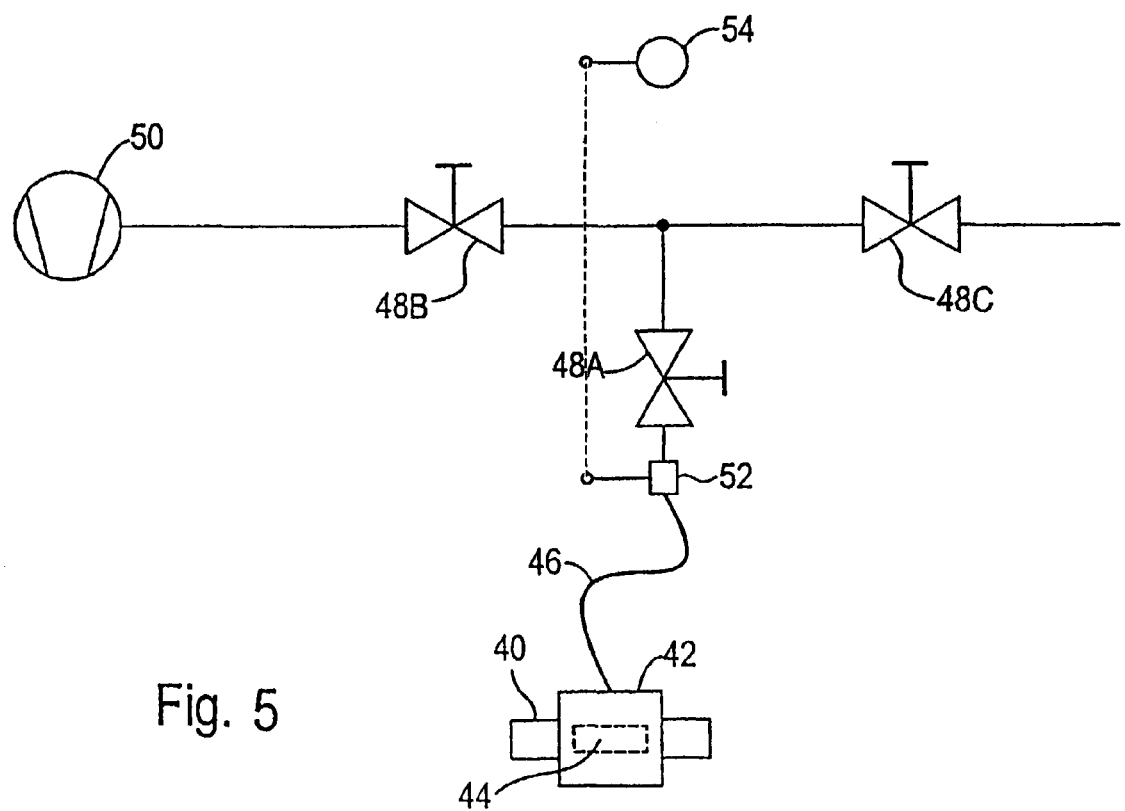
FIG. 5 is a schematic and block circuit diagram of a structure for determining air permeability (leak rate) of the gastight layer according to the invention.

To determine the leak rate $q_L$, a procedure illustrated in FIG. 5 is followed. A specimen 40, for example, a tubular porous cathode 16 for a fuel cell 18 with the electrolyte layer 14 applied to it, is introduced into a special adapter 42. The adapter 42 has a window 44 with a defined area F and completely seals the specimen 40 with respect to the environment apart from the window 44. Air is pumped out of the cavity in the tubular specimen 40 through a first valve 48A and a second valve 48B through a pump line 46 by a pump 50, and a subatmospheric pressure is generated. When a set sub-atmospheric pressure is reached, the valves 48B, 48A are closed and the profile of the pressure rise is recorded based upon the leakage area defined by the window 44, by a pressure gauge 52. The pressure profile is evaluated by an evaluation unit 54. There is a further valve 48C available for venting following the measurement cycle.

To determine the leak rate $q_L$, the pressure rise over a measurement time dt of 30 to 600 s is recorded. The differential pressure that was initially established (pressure reduction between the cavity in the specimen and the external environment) is 1 bar, the measurement takes place at room temperature, and the test gas is air.

With such a measurement structure, a specific leak rate $q_{LF}$ of approximately $2 \cdot 10^{-4}$ mbar·l/s·cm² is determined for a gastight layer 12 that has been applied using the process described above.

We claim:

1. A method for producing a solid electrolyte layer, of a fully stabilized zirconium oxide layer on a substrate, which comprises:
   applying a zirconium oxide starting material to the substrate together with a sintering additive as a green layer, the sintering additive being boron nitride;
   forming a liquid phase of the sintering additive by subsequently heating the sintering additive; and
   densifying the green layer with a liquid-phase sintering operation at a reduced sintering temperature as compared to a sintering temperature required without the sintering additive.

2. The method according to claim 1, which further comprises selecting process parameters, including at least one of heating rate, sintering temperature, and holding time, to cause the liquid phase to still be present when the reduced sintering temperature is reached and to cause the
   densified layer to be substantially free of sintering additive.

3. The method according to claim 1, which further comprises setting a maximum sintering temperature of less than 1,400° C.

4. The method according to claim 1, which further comprises setting a maximum sintering temperature of less than 1,300° C.

5. The method according to claim 1, which further comprises setting a maximum sintering temperature to a value between approximately 1,100° C. and approximately 1,300° C.

6. The method according to claim 1, which further comprises setting a heating rate of approximately 4 to approximately 7 K/min.

7. The method according to claim 1, which further comprises applying to the substrate:
  a green layer including the sintering additive; and
  a zirconium oxide layer that does not include the sintering additive.

8. The method according to claim 1, which further comprises forming a gastight zirconium oxide layer with a porosity of less than 5% by volume.

9. The method according to claim 8, which further comprises forming the gastight layer with a layer thickness of between approximately 5 and approximately 300 µm.

10. The method according to claim 8, which further comprises forming the gastight layer with an air permeability of $\leq 10^{-3}$ mbar·l/s·cm$^2$.

11. The method according to claim 8, which further comprises forming the gastight layer with an air permeability of approximately $2 \cdot 10^{-4}$ mbar·l/s·cm$^2$.

12. The method according to claim 8, which further comprises:
  providing a fuel cell having an electrode; and
  coating the electrode with the zirconium oxide layer as a solid electrolyte layer.

13. The method according to claim 8, which further comprises:
  providing a gas sensor; and
  applying the zirconium oxide layer to the gas sensor as a solid electrolyte layer.

14. A method for producing a solid electrolyte layer, of a fully stabilized zirconium oxide layer on a substrate, which comprises:
  applying to the substrate a green layer including a sintering additive and a zirconium oxide layer that does not include the sintering additive;
  forming a liquid phase of the sintering additive by subsequently heating the sintering additive; and
  densifying the green layer to form a densified layer with a liquid-phase sintering operation at a reduced sintering temperature compared to a sintering temperature required without the sintering additive, in which operation process parameters, including at least one of heating rate, sintering temperature, and holding time, are selected to cause the liquid phase to still be present when the reduced sintering temperature is reached and to cause the densified layer to be substantially free of the sintering additive, the reduced sintering temperature being higher than a sintering temperature required for a sintering operation with sintering additive.

15. The method according to claim 14, which further comprises setting a maximum sintering temperature of less than 1,400° C.

16. The method according to claim 14, which further comprises setting a maximum sintering temperature of less than 1,300° C.

17. The method according to claim 14, which further comprises setting a maximum sintering temperature to a value between approximately 1,100° C. and approximately 1,300° C.

18. The method according to claim 14, which further comprises setting a heating rate of approximately 4 to approximately 7 K/min.

19. The method according to claim 14, which further comprises forming a gastight zirconium oxide layer with a porosity of less than 5% by volume.

20. The method according to claim 19, which further comprises forming the gastight layer with a layer thickness of between approximately 5 and approximately 100 µm.

21. The method according to claim 19, which further comprises forming the gastight layer with an air permeability of $\leq 10^{-3}$ mbar·l/s·cm$^2$.

22. The method according to claim 19, which further comprises forming the gastight layer with an air permeability of approximately $2 \cdot 10^{-4}$ mbar·l/s·cm$^2$.

23. The method according to claim 19, which further comprises:
  providing a fuel cell having an electrode; and
  coating the electrode with the zirconium oxide layer as a solid electrolyte layer.

24. The method according to claim 19, which further comprises:
  providing a gas sensor; and
  applying the zirconium oxide layer to the gas sensor as a solid electrolyte layer.

25. A method for producing a solid electrolyte layer, of a fully stabilized zirconium oxide layer on a substrate, which comprises:
  applying to the substrate:
    a zirconium oxide starting material as a green layer with the sintering additive; and
    a zirconium oxide starting material as a green layer without the sintering additive;
  forming a liquid phase of the sintering additive by subsequently heating the sintering additive; and
  densifying the green layer with a liquid-phase sintering operation at a reduced sintering temperature compared to a sintering temperature required without the sintering additive.

26. The method according to claim 25, which further comprises selecting process parameters, including at least one of heating rate, sintering temperature, and holding time, to cause the liquid phase to still be present when the reduced sintering temperature is reached and to cause the densified layer to be substantially free of sintering additive.

27. The method according to claim 25, which further comprises setting a maximum sintering temperature of less than 1,400° C.

28. The method according to claim 25, which further comprises setting a maximum sintering temperature of less than 1,300° C.

29. The method according to claim 25, which further comprises setting a maximum sintering temperature to a value between approximately 1,100° C. and approximately 1,300° C.

30. The method according to claim 25, which further comprises setting a heating rate of approximately 4 to approximately 7 K/min.

31. The method according to claim 25, which further comprises applying to the substrate:
  a green layer including the sintering additive; and
  a zirconium oxide layer that does not include the sintering additive.

32. The method according to claim 25, which further comprises forming a gastight zirconium oxide layer with a porosity of less than 5% by volume.

33. The method according to claim 32, which further comprises forming the gastight layer with a layer thickness of between approximately 5 and approximately 100 µm.

34. The method according to claim 32, which further comprises forming the gastight layer with an air permeability of $\leq 10^{-3}$ mbar·l/s·cm$^2$.

35. The method according to claim 32, which further comprises forming the gastight layer with an air permeability of approximately $2 \cdot 10^{-4}$ mbar·l/s·cm².

36. The method according to claim 32, which further comprises:
- providing a fuel cell having an electrode; and
- coating the electrode with the zirconium oxide layer as a solid electrolyte layer.

37. The method according to claim 32, which further comprises:
- providing a gas sensor; and
- applying the zirconium oxide layer to the gas sensor as a solid electrolyte layer.

* * * * *